United States Patent
Burton et al.

(10) Patent No.: US 11,851,411 B2
(45) Date of Patent: Dec. 26, 2023

(54) HERBICIDAL COMPOUNDS

(71) Applicant: SYNGENTA CROP PROTECTION AG, Basel (CH)

(72) Inventors: Paul Matthew Burton, Bracknell (GB); Alexander Martin Richard Smith, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 552 days.

(21) Appl. No.: 17/253,165

(22) PCT Filed: Jun. 18, 2019

(86) PCT No.: PCT/EP2019/066077
§ 371 (c)(1),
(2) Date: Dec. 17, 2020

(87) PCT Pub. No.: WO2019/243358
PCT Pub. Date: Dec. 26, 2019

(65) Prior Publication Data
US 2021/0276962 A1    Sep. 9, 2021

(30) Foreign Application Priority Data
Jun. 19, 2018  (GB) .................................. 1810047

(51) Int. Cl.
*C07D 257/06*     (2006.01)
*A01N 25/32*      (2006.01)
*A01N 43/713*     (2006.01)
*A01N 43/82*      (2006.01)
*C07D 271/113*    (2006.01)

(52) U.S. Cl.
CPC ............ *C07D 257/06* (2013.01); *A01N 25/32* (2013.01); *A01N 43/713* (2013.01); *A01N 43/82* (2013.01); *C07D 271/113* (2013.01)

(58) Field of Classification Search
CPC ................................................... C07D 257/06
See application file for complete search history.

(56) References Cited

FOREIGN PATENT DOCUMENTS

| WO | 2012028579 A1 | 3/2012 |
|----|---------------|--------|
| WO | 2012126932 A1 | 9/2012 |
| WO | 2017102275 A1 | 6/2017 |
| WO | 2017205396 A1 | 11/2017 |

OTHER PUBLICATIONS

Written Opinion of the International Searching Authority and International Search Report for PCT/EP2019/066077, dated Sep. 25, 2019.

*Primary Examiner* — Robert A Wax
*Assistant Examiner* — John Seungjai Kwon
(74) *Attorney, Agent, or Firm* — BakerHostetler; Toni-Junell Herbert

(57) ABSTRACT

The present invention relates to compounds Formula (I): wherein Q, $R^2$, $R^3$, $R^4$ and $R^5$ are as defined herein. The invention further relates to compositions comprising said compounds, and methods of controlling weeds using said compounds and/or compositions.

14 Claims, No Drawings

HERBICIDAL COMPOUNDS

CROSS-REFERENCE TO RELATED APPLICATIONS

This application is a 371 National Stage application of International Application No. PCT/EP2019/066077 filed Jun. 18, 2019, which claims priority to GB 1810047.9, filed Jun. 19, 2018, the entire contents of these applications are hereby incorporated by reference.

The present invention relates to novel herbicidal compounds, to processes for their preparation, to herbicidal compositions which comprise the novel compounds, and to their use for controlling weeds, in particular in crops of useful plants, or for inhibiting plant growth.

N-(tetrazol-5-yl)- and N-(1,3,4-oxadiazol-2-yl) arylcarboxamides are disclosed in, for example, WO2012/028579 and WO2012/126932 respectively. The present invention relates to novel arylcarboxamides.

Thus, according to the present invention there is provided a compound of Formula (I):

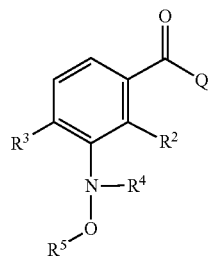

(I)

or an agronomically acceptable salt thereof, wherein:—
Q is selected from the group consisting of Q1 and Q2:

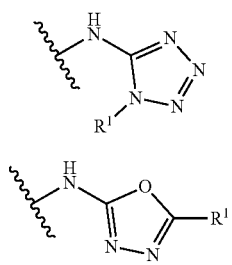

Q1

Q2

$R^1$ is selected from the group consisting of $C_1$-$C_4$alkyl-, $C_1$-$C_4$haloalkyl- and $C_1$-$C_4$alkoxy-$C_1$-$C_4$alkyl-;
$R^2$ is selected from the group consisting of halogen, $C_1$-$C_6$alkyl-, $C_1$-$C_3$alkoxy-, $C_1$-$C_6$ haloalkyl-, $C_1$-$C_3$haloalkoxy- and —S(O)$_p$C$_1$-$C_6$alkyl;
$R^3$ is selected from the group consisting of halogen, $C_1$-$C_6$alkyl-, $C_1$-$C_3$alkoxy-, $C_1$-$C_6$ haloalkyl-, $C_1$-$C_3$haloalkoxy- and —S(O)$_p$C$_1$-$C_6$alkyl;
$R^4$ is selected from the group consisting of $C_1$-$C_6$alkyl, $C_1$-$C_6$alkyl-C(O)—, $C_1$-$C_6$alkoxy-C(O)—;
$R^5$ is $C_1$-$C_6$alkyl- or $C_1$-$C_6$haloalkyl; and
p=0, 1 or 2.

$C_1$-$C_6$alkyl and $C_1$-$C_4$alkyl groups include, for example, methyl (Me, CH$_3$), ethyl (Et, C$_2$H$_5$), n-propyl (n-Pr), isopropyl (i-Pr), n-butyl (n-Bu), isobutyl (i-Bu), sec-butyl and tert-butyl (t-Bu).

Halogen (or halo) encompasses fluorine, chlorine, bromine or iodine. The same correspondingly applies to halogen in the context of other definitions, such as haloalkyl.

$C_1$-$C_6$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl-, heptafluoro-n-propyl and perfluoro-n-hexyl. $C_1$-$C_4$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl- and heptafluoro-n-propyl-.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

In one embodiment of the present invention there is provided a compound of Formula (I) wherein Q is Q1 (shown below as a Compound of Formula (Ia)). In another embodiment of the present invention there is provided a compound of Formula (I) wherein Q is Q2 (shown below as a Compound of Formula (Ib)).

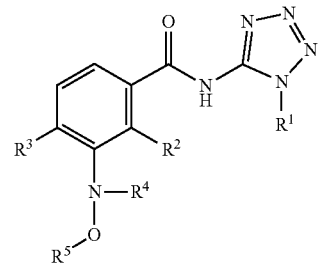

(Ia)

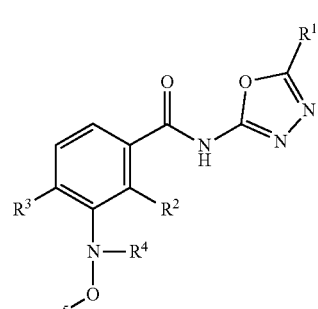

(Ib)

In a preferred aspect of the present invention $R^1$ is selected from the group consisting of methyl, ethyl and n-propyl, especially methyl.

In one embodiment of the present invention, $R^2$ is $C_1$-$C_6$alkyl- (preferably methyl) or halogen (preferably chlorine). In a preferred embodiment, $R^2$ is chlorine.

In one embodiment of the present invention, $R^3$ is $C_1$-$C_6$ haloalkyl (preferably $CF_3$) or —$S(O)_pC_1$-$C_6$ alkyl (preferably —$SO_2CH_3$).

In one embodiment of the present invention, $R^4$ is selected from the group consisting of $C_1$-$C_6$alkyl (preferably methyl), $C_1$-$C_6$alkyl-C(O)— (preferably $CH_3C(O)$—), $C_1$-$C_4$alkoxy-C(O)— (preferably $CH_3O(O)C$—, $C_2H_5O(O)C$— or t-BuO(O)C—).

In one embodiment of the present invention, $R^5$ is methyl.

In one embodiment of the present invention are provided compounds of Formula (I) wherein $R^4$ is $CH_3C(O)$— and $R^5$ is methyl.

The present invention also includes agronomically acceptable salts that the compounds of Formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound of the present invention and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumicloracpentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chloride, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), I+4-hydroxy-1-methoxy-5-methyl-3-[4-(trifluoromethyl)-2-pyridyl]imidazolidin-2-one, I+4-hydroxy-1,5-dimethyl-3-[4-(trifluoromethyl)-2-pyridyl]imidazolidin-2-one, I+5-ethoxy-4-hydroxy-1-methyl-3-[4-(trifluoromethyl)-2-pyridyl]imidazolidin-2-one, I+4-hydroxy-1-methyl-3-[4-(trifluoromethyl)-2-pyridyl]imidazolidin-2-one, I+4-hydroxy-1,5-dimethyl-3-[1-methyl-5-(trifluoromethyl)pyrazol-3-yl]imidazolidin-2-one, I+(4R)1-(5-tert-butylisoxazol-3-yl)-4-ethoxy-5-hydroxy-3-methyl-imidazolidin-2-one, 3-[2-(3,4-dimethoxyphenyl)-6-methyl-3-oxo-pyridazine-4-carbonyl]bicyclo[3.2.1]octane-2,4-dione, I+2-[2-(3,4-dimethoxyphenyl)-6-methyl-3-oxo-pyridazine-4-carbonyl]-5-methyl-cyclohexane-1,3-dione, I+2-[2-(3,4-dimethoxyphenyl)-6-methyl-3-oxo-pyridazine-4-carbonyl]cyclohexane-1,3-dione, 2-[2-(3,4-dimethoxyphenyl)-6-methyl-3-oxo-pyridazine-4-carbonyl]-5,5-dimethyl-cyclohexane-1,3-dione, I+6-[2-(3,4-dimethoxyphenyl)-6-methyl-3-oxo-pyridazine-4-carbonyl]-2,2,4,4-tetramethyl-cyclohexane-1,3,5-trione, I+2-[2-(3,4-dimethoxyphenyl)-6-methyl-3-oxo-pyridazine-4-carbonyl]-5-ethyl-cyclohexane-1,3-dione, I+2-[2-(3,4-dimethoxyphenyl)-6-methyl-3-oxo-pyridazine-4-carbonyl]-4,4,6,6-tetramethyl-cyclohexane-1,3-dione, I+2-[6-cyclopropyl-2-(3,4-dimethoxyphenyl)-3-oxo-pyridazine-4-carbonyl]-5-methyl-cyclohexane-1,3-dione, I+3-[6-cyclopropyl-2-(3,4-dimethoxyphenyl)-3-oxo-pyridazine-4-carbonyl]bicyclo[3.2.1]octane-2,4-dione, I+2-[6-cyclopropyl-2-(3,4-dimethoxyphenyl)-3-oxo-pyridazine-4-carbonyl]-5,5-dimethyl-cyclohexane-1,3-dione, I+6-[6-cyclopropyl-2-(3,4-dimethoxyphenyl)-3-oxo-pyridazine-4-carbonyl]-2,2,4,4-tetramethyl-cyclohexane-1,3,5-trione, I+2-[6-cyclopropyl-2-(3,4-dimethoxyphenyl)-3-oxo-pyridazine-4-carbonyl]cyclohexane-1,3-dione, I+4-[2-(3,4-dimethoxyphenyl)-6-methyl-3-oxo-pyridazine-4-carbonyl]-2,2,6,6-tetramethyl-tetrahydropyran-3,5-dione and 4-[6-cyclopropyl-2-(3,4-dimethoxyphenyl)-3-oxo-pyridazine-4-carbonyl]-2,2,6,6-tetramethyl-tetrahydropyran-3,5-dione.

The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl) amino]benzenesulfonamide.

The safeners of the compound of Formula I may also be in the form of esters or salts, as mentioned e.g. in The Pesticide Manual, 16$^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of controlling weeds at a locus said method comprising application to the locus of a weed controlling amount of a composition comprising a compound of Formula (I). Moreover, the present invention further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow. Some crop plants may be inherently tolerant to herbicidal effects of compounds of Formula (I). However, in some instances tolerance may need to be engineered into the crop plant, for example by way of genetic engineering. Thus, it is possible that the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species. Several HPPD-tolerant soybean transgenic "events" are known, and include for example SYHT04R (WO2012/082542), SYHT0H2 (WO2012/082548) and FG72. Other polynucleotide sequences that can be used to provide plants which are tolerant to the compounds of the present invention are disclosed in, for example, WO2010/085705 and WO2011/068567. Crop plants in which the composition according to the invention can be used thus include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared according to the following schemes. Amides of formula (I) may be prepared from benzoic acids of formula (II) and amines of formula (III) or formula (IV).

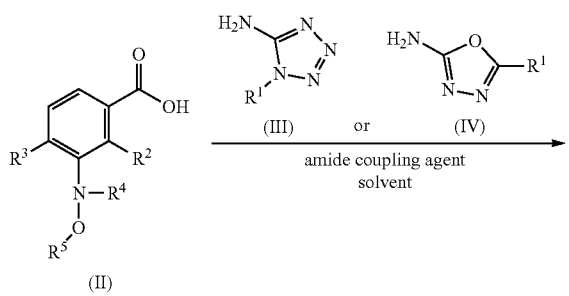

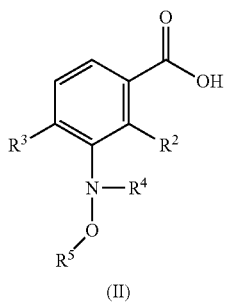

(II)

Where "Alk" is defined as a $C_1$-$C_6$ alkyl group.

The ester of formula (V) is treated with a hydroxide base such as lithium hydroxide in a suitable solvent mixture, for example a 3:1 mixture of ethanol and water.

Esters of formula (V) may be prepared by a variety of methods depending on the nature of $R^4$ and $R^5$.

Where $R^4$ is alkyl, compounds of formula (V) may be prepared by alkylation of compounds of formula (VI).

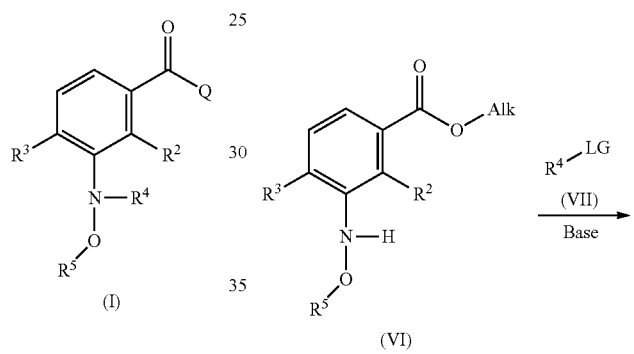

To prepare compounds of formula (I) where Q=Q1, the benzoic acid of formula (II) and amine of formula (III) are reacted by using an amide coupling agent such as N,N'-carbonyldiimidazole or propylphosphonic anhydride in a suitable solvent such as 1,4-dioxane or N,N-dimethylformamide.

To prepare compounds of formula (I) where Q=Q2, the benzoic acid of formula (II) and amine of formula (IV) are reacted by using an amide coupling agent such as N,N'-carbonyldiimidazole or propylphosphonic anhydride in a suitable solvent such as 1,4-dioxane or N,N-dimethylformamide.

Benzoic acids of formula (II) may be prepared from esters of formula (V).

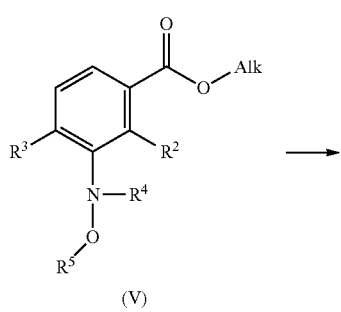

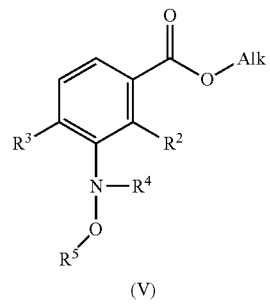

(V)

The compound of formula (VI) may be treated with an alkylating agent of formula (VII) in the presence of a suitable base and a suitable solvent. LG is defined as a leaving group, for example iodide, bromide, chloride, tosylate, mesylate or —OSO$_2$Me. For example, where $R^4$ is methyl, (VII) could be dimethylsulfate. An example of a suitable base is n-butyl lithium. An example of a suitable solvent is tetrahydrofuran.

Compounds of formula (VI) may be prepared by Boc-deprotection of compounds of formula VIII under acidic conditions.

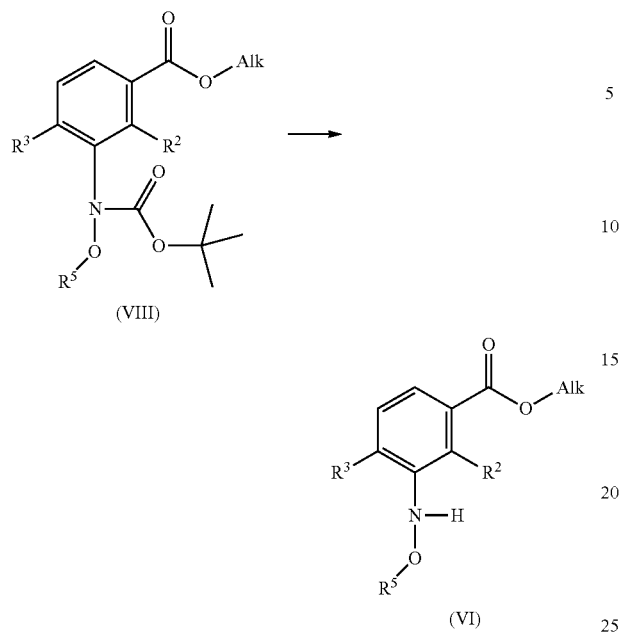

(VIII)

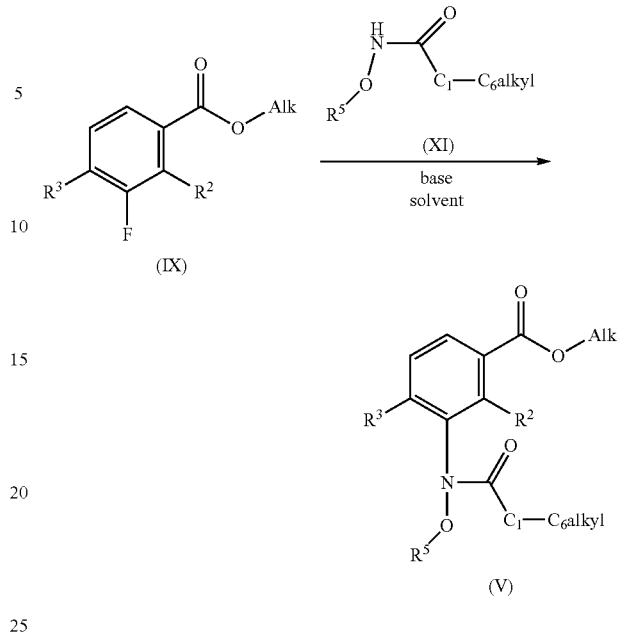

(VI)

The compound of formula (VIII) is treated with a suitable acid, for example hydrochloric acid.

The reaction may use a solvent or it may use the suitable acid itself as the solvent.

Compounds of formula (VIII) may be prepared from fluoroarenes of formula (IX) and compounds of formula (X).

The fluoroarene of formula (IX) is treated with a compound of formula (XI) in the presence of a suitable base, for example potassium carbonate, in a suitable solvent, for example N,N-dimethylacetamide.

Where $R^4$ is $C_1$-$C_6$alkyl-OC(=O)—, compounds of formula (V) may be prepared by treating compounds of formula (VI) with an alkyl chloroformate of formula (VII).

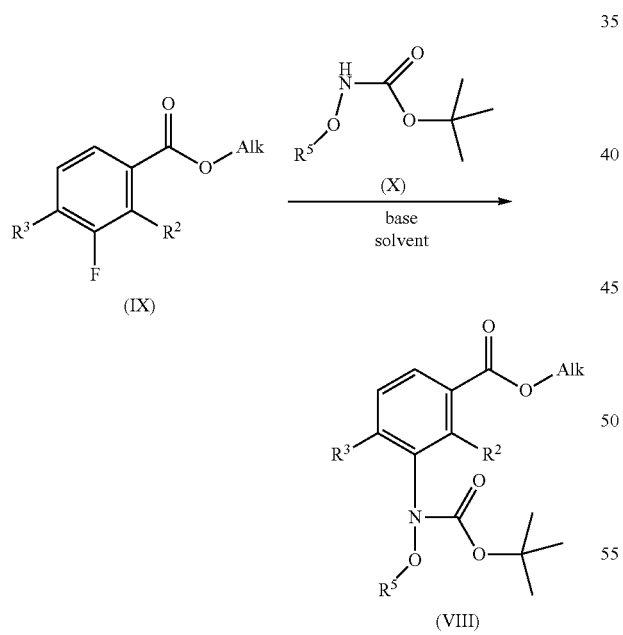

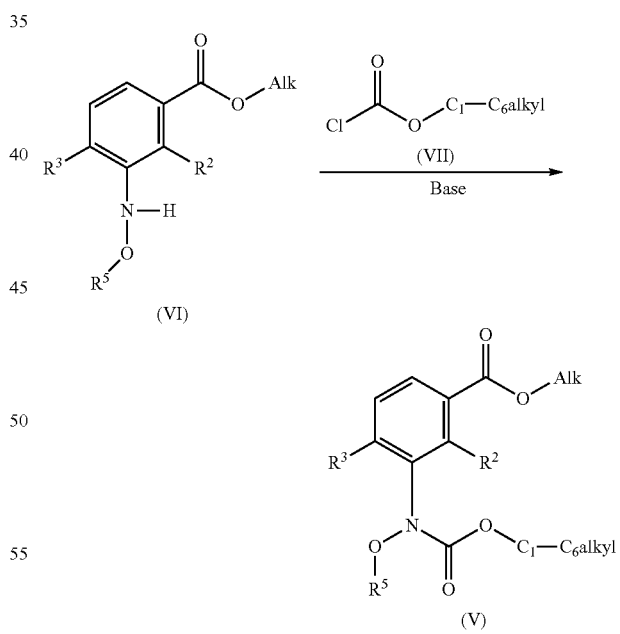

The compound of formula (IX) is treated with the compound of formula (X) in the presence of a suitable base, for example potassium carbonate, and a suitable solvent, for example N,N-dimethylacetamide.

Where $R^4$ is $C_1$-$C_6$alkyl-C(=O)—, compounds of formula (V) may be prepared by reaction of fluoroarenes of formula (IX) with compounds of formula (XI).

The compound of formula (VI) is treated with the alkyl chloroformate of formula (VII), a suitable base, for example sodium hydride, in a suitable solvent, for example tetrahydrofuran to give the compound of formula (V).

Compounds of formula (V) where $R^2$ is alkyl (formula Vb), may be prepared by reaction of chloroarenes of formula (Va) with an alkyl boronic acid.

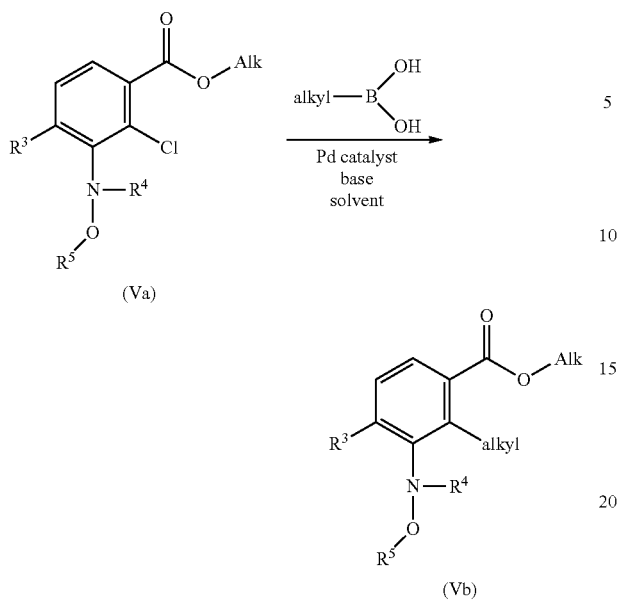

The chloroarene of formula (Va) is treated with the alkyl boronic acid in the presence of a suitable base, for example potassium carbonate, in a suitable solvent, for example 1,4-dioxane and with a suitable palladium catalyst. An example of a suitable palladium catalyst is [1,3-Bis(2,6-Diisopropylphenyl)imidazol-2-ylidene](3-chloropyridyl)palladium(II) dichloride.

The following non-limiting examples provide specific synthesis methods for representative compounds of the present invention, as referred to the Tables provided herein.

PREPARATIVE EXAMPLE 1: PREPARATION OF COMPOUND 1.001

Step 1. Preparation of 2-chloro-3-fluoro-4-(trifluoromethyl)benzoic Acid

A solution of N,N,N',N'-tetramethylethylenediamine (26 mL, 170 mmol) in dry tetrahydrofuran (56 mL) was cooled to −78° C. N-butyllithium (2.5 M in hexanes, 67 mL, 170 mmol) was added dropwise over 10 min, then stirring was continued for 5 min. A solution of 3-fluoro-4-(trifluoromethyl)benzoic acid (14 g, 67 mmol) in tetrahydrofuran (56 mL) was added dropwise over 1 h, maintaining the internal temperature below −70° C. The mixture was stirred for a further 1.5 h at −78° C. A solution of 1,1,1,2,2,2-hexachloroethane (39.8 g, 168 mmol) in tetrahydrofuran (56 mL) was added dropwise over 20 min, maintaining the internal temperature below −50° C., and the resulting mixture stirred at −70° C. for 45 min.

The cold bath was removed and the reaction mixture allowed to warm to −20° C. over 30 min. HCl (2 M, 400 ml) was added over 5 min (via dropping funnel). The resulting exotherm raised the internal temp to 20° C. The mixture was extracted with ethyl acetate (2×200 ml). The combined extracts were washed with brine (100 ml), dried (MgSO$_4$) and concentrated. The crude was triturated with isohexane (100 ml), collecting the solid by filtration to give 2-chloro-3-fluoro-4-(trifluoromethyl)benzoic acid (14 g, 86% Yield) as a brown solid. $^1$H NMR (400 MHz, chloroform) δ=8.80 (br s, 1H), 7.91 (dd, J=0.6, 8.3 Hz, 1H), 7.64 (dd, J=6.5, 8.1 Hz, 1H).

Step 2. Preparation of ethyl 2-chloro-3-fluoro-4-(trifluoromethyl)benzoate

To a flask equipped with a condenser and gas bubbler was added 2-chloro-3-fluoro-4-(trifluoromethyl)benzoic acid (29.1 g, 120 mmol) and triethyl orthoformate (233 mL). The mixture was heated to 140° C. for 11 h. The mixture was concentrated in vacuo then azeotroped with toluene 3 times to give ethyl 2-chloro-3-fluoro-4-(trifluoromethyl)benzoate (31.4 g) s a colourless oil. $^1$H NMR (400 MHz, chloroform) δ=7.68 (dd, J=0.7, 8.3 Hz, 1H), 7.57 (dd, J=6.6, 7.9 Hz, 1H), 4.45 (q, J=7.1 Hz, 2H), 1.42 (t, J=7.2 Hz, 3H).

Step 3. Preparation of 3-[acetyl(methoxy)amino]-2-chloro-4-(trifluoromethyl)benzoate To a multi-necked flask equipped with a thermometer, nitrogen inlet and reflux condenser was added ethyl 2-chloro-3-fluoro-4-(trifluoromethyl)benzoate (25 g, 92.3 mmol), N-methoxyacetamide (12.4 g, 138.6 mmol) and N,N-dimethylacetamide (200 mL). The reaction was stirred under nitrogen and potassium carbonate (25.5 g, 184.8 mmol) was added in 5 g portions over 10 min. The mixture was heated to 100° C. for 5 h.

The reaction mixture was cooled and poured into a 2 L separator containing EtOAc (450 ml) and water (450 ml). The aqueous layer was separated and further extracted with EtOAc (225 ml). The combined organics were washed with water (450 ml) then brine (200 ml), dried (Na$_2$SO$_4$) and concentrated. The crude was purified by flash chromatography (Silica: 2×330 g, Solvent: isohexane/ethyl acetate, gradient: 10-20%) to give ethyl 3-[acetyl(methoxy)amino]-2-chloro-4-(trifluoromethyl)benzoate (20.3 g) as a colourless oil that solidified upon standing.

$^1$H NMR (400 MHz, chloroform, rotameric) δ=7.98-7.84 (m, 1H), 7.83-7.67 (m, 1H), 4.52-4.36 (m, 2H), 3.98-3.69 (m, 3H), 2.57-1.80 (m, 3H), 1.48-1.36 (m, 3H). 19F NMR (376 MHz, chloroform, rotameric) δ=−60.25 (s), −61.09 (s)

Step 4. Preparation of 3-[acetyl(methoxy)amino]-2-chloro-4-(trifluoromethyl)benzoic Acid To a flask was added ethyl 3-[acetyl(methoxy)amino]-2-chloro-4-(trifluoromethyl)benzoate (20.3 g, 59.8 mmol) and tetrahydrofuran (203 mL) and the solution was cooled in an ice bath. A solution of lithium hydroxide (4.38 g, 179 mmol) in water (203 mL) was added dropwise over 5 min maintaining the internal temp below 20° C. The cold bath was removed and the mixture stirred for 15 min. The mixture was concentrated to remove THF then partitioned between EtOAc (200 ml) and water (200 ml). The aqueous layer was separated, acidified with HCl (2 M, 200 ml) and extracted to DCM (2×200 ml). The combined extracts were dried (MgSO$_4$) and concentrated to give 3-[acetyl(methoxy)amino]-2-chloro-4-(trifluoromethyl)benzoic acid (18.2 g) as a white solid.

Step 5. Preparation of 3-[acetyl(methoxy)amino]-2-chloro-N-(1-methyltetrazol-5-yl)-4-(trifluoromethyl)benzamide To a flask was added 3-[acetyl(methoxy)amino]-2-chloro-4-(trifluoromethyl)benzoic acid (15 g, 48.1 mmol) and 1,4-dioxane (225 mL). The mixture was heated to 90° C. and 1,1'-carbonyldiimidazole (10.3 g, 62.5 mmol) was added in several small portions over 30 min, then stirred for a further 30 min. The mixture was cooled to room temperature and charged with 1-methyltetrazol-5-amine (6.2 g, 62.6 mmol) and 1,8-diazabicyclo[5.4.0]undec-7-ene (7.35 mL, 48.1 mmol). The mixture was heated to 90° C. for 2 h. The mixture was cooled then concentrated and the residue dissolved in EtOAc (200 ml). The solution was placed in an ice bath and HCl (2 M, 200 ml) was added in portions, maintaining the temperature below 20° C. The mixture was transferred to a 1 L separating funnel. The organic layer was separated, washed with HCl (2 M, 200 ml) then brine (100 ml), dried (MgSO4) and concentrated. The crude was purified by flash chromatography (Silica: 330 g, Solvent: isohexane/EtOAc, Gradient: 50-100%) to give 3-[acetyl (methoxy)amino]-2-chloro-N-(1-methyltetrazol-5-yl)-4-(trifluoromethyl)benzamide (17.8 g) as a foaming white solid. $^1$H NMR (400 MHz, chloroform, rotameric) δ=11.11 (br s, 1H), 7.96-7.59 (m, 2H), 4.16-4.01 (m, 3H), 3.89-3.76 (m, 3H), 2.34-1.85 (m, 3H)

PREPARATIVE EXAMPLE 2: PREPARATION OF COMPOUND 2.009

Step 1. Preparation of 3-[tert-butoxycarbonyl (methoxy)amino]-2-chloro-4-(trifluoromethyl)benzoate To a flask was added tert-butyl N-methoxycarbamate (1.1 mL, 7.2 mmol) and N,N-dimethylacetamide (11 ml). The mixture was cooled to 0° C. and potassium tert-butoxide (0.76 g, 6.7 mmol) was added in several small portions over 5 min. The mixture was stirred for 5 minutes at 0° C. before warming to room temperature for a further 15 min. Ethyl 2-chloro-3-fluoro-4-(trifluoromethyl)benzoate (1.5 g, 5.5 mmol) in N,N-dimethylacetamide (11 mL) was added in a single portion and the reaction mixture heated to 80° C. for 30 min. The mixture was cooled, quenched with citric acid (10%) and extracted to EtOAc. The extracts were dried (Na$_2$SO$_4$) and concentrated. The crude was purified by flash chromatography (Silica: 80 g, Solvent: isohexane/ethyl acetate, Gradient: 5-10%) to give ethyl 3-[tert-butoxycarbonyl(methoxy)amino]-2-chloro-4-(trifluoromethyl)benzoate (1.37 g) as a colourless oil. 1H NMR (400 MHz, chloroform, rotameric) δ=7.84 (d, J=8.2 Hz, 1H), 7.67 (d, J=8.3 Hz, 1H), 4.45 (br dd, J=3.9, 7.1 Hz, 2H), 3.91-3.81 (m, 3H), 1.60-1.34 (m, 12H).

Step 2. Preparation of 3-[tert-butoxycarbonyl (methoxy)amino]-2-chloro-4-(trifluoromethyl)benzoic Acid To a flask was added ethyl 3-[tert-butoxycarbonyl (methoxy)amino]-2-chloro-4-(trifluoromethyl)benzoate (1 g, 2.51 mmol), tetrahydrofuran (10 mL), water (5 mL) and lithium hydroxide (323 mg, 7.54 mmol). The mixture was stirred for 2 h at room temperature. The mixture was concentrated to remove THF, then washed with EtOAc. The aqueous layer was acidified with citric acid (10%), extracted to DCM and concentrated to give 3-[tert-butoxycarbonyl (methoxy)amino]-2-chloro-4-(trifluoromethyl)benzoic acid (921 mg) as a white solid. 1H NMR (400 MHz, chloroform, rotameric) δ=7.98-7.94 (m, 1H), 7.94-7.89 (m, 1H), 3.74 (s, 3H), 1.58-1.22 (m, 9H).

Step 3. Preparation of tert-butyl N-[2-chloro-3-[(5-methyl-1,3,4-oxadiazol-2-yl)carbamoyl]-6-(trifluoromethyl)phenyl]-N-methoxy-carbamate To a solution of 3-[tert-butoxycarbonyl(methoxy)amino]-2-chloro-4-(trifluoromethyl)benzoic acid (0.65 g, 1.76 mmol in dichloromethane (9.75 mL) and N,N-dimethylformamide (13.7 µL, 0.176 mmol) was added oxalyl dichloride (306 µL, 3.52 mmol), dropwise. The resulting mixture was stirred for 1 h to give a stock solution of acid chloride. 5 ml (half) of the acid chloride solution was concentrated (at <30° C. to avoid risk of Boc cleavage) and the residue was dissolved in 1,4-dioxane (6.8 mL). The mixture was charged with 5-methyl-1,3,4-oxadiazol-2-amine (0.131 g, 1.32 mmol, 100 mass %) and 1-methylimidazole (0.140 mL, 1.76 mmol) and heated to 100° C. for 2 h. The mixture was concentrated and the residue purified by preparative HPLC. The desired fractions were freeze dried to give tert-butyl N-[2-chloro-3-[(5-methyl-1,3,4-oxadiazol-2-yl)carbamoyl]-6-(trifluoromethyl)phenyl]-N-methoxy-carbamate (0.147 g) as a white solid. 1H NMR (400 MHz, chloroform, rotameric) δ=7.84 (br d, J=8.2 Hz, 1H), 7.71 (d, J=8.3 Hz, 1H), 3.92-3.75 (m, 3H), 2.55 (s, 3H), 1.64-1.31 (m, 9H).

PREPARATIVE EXAMPLE 3: PREPARATION OF COMPOUND 1.012

Step 1. Preparation of 1-bromo-2-chloro-3-fluoro-4-methylsulfanyl-benzene

1-Chloro-2-fluoro-3-methylsulfanyl-benzene (7.50 g, 42.5 mmol) was dissolved in CH$_2$Cl$_2$ (75.0 mL). FeCl$_3$ (0.344 g, 2.12 mmol) and Br$_2$ (2.83 mL, 55.2 mmol) were added to it and was heated at 50° C. for 5 h. The reaction mixture was partitioned between DCM-water and the organic layer was dried over Na$_2$SO$_4$. The solvent was evaporated and the crude residue was purified by chromatography using hexane as eluent to give 1-bromo-2-chloro-3-fluoro-4-methylsulfanyl-benzene (8.1 g, 32 mmol) as a solid. 1H NMR (400 MHz, CDCl$_3$) 7.34-7.37 (dd, 1H), 7.00-7.04 (app, t, 1H), 2.46 (s, 3H).

Step 2. Preparation of 1-bromo-2-chloro-3-fluoro-4-methylsulfonyl-benzene mCPBA (77 wt %, 15.6 g, 69.5 mmol) was added to a stirred solution of 1-bromo-2-chloro-3-fluoro-4-methylsulfanyl-benzene (7.10 g, 27.8 mmol) in DCM (100 mL) at 0° C. The reaction mixture was then stirred at RT for 16 h, then was washed with 5% sodium metabisulfite. The solid was filtered through celite and the filtrate was washed with sat. NaHCO$_3$ and then water.

The organic layer was dried over Na2SO4. The solvent was evaporated to give a crude oil, which was purified with 30% Acetone-DCM to give 1-bromo-2-chloro-3-fluoro-4-methylsulfonyl-benzene (6.78 g, 23.6 mmol) as white solid. 1H NMR (400 MHz, CDCl3) 7.72-7.76 (m, 1H), 7.63-7.65 (m, 1H), 3.23 (s, 3H).

Step 3. Preparation of ethyl 2-chloro-3-fluoro-4-methylsulfonyl-benzoate 1-bromo-2-chloro-3-fluoro-4-methylsulfonyl-benzene (1.30 g, 4.52 mmol) was charged into a 100 mL autoclave vessel. Ethanol (30.0 mL) was added and the solution was degassed with argon for 15 min. Triethylamine (1.58 mL, 11.3 mmol), dppb (193 mg, 0.452 mmol) and palladium acetate (50 mg, 0.23 mmol) were added and the mixture was sparged with CO. The autoclave was heated at 100° C. under 300 psi CO pressure for 16 h. The vessel was depressurized and the reaction mixture was evaporated, made acidic with 1N HCl and extracted with DCM (20 mL×2). The organic layer was dried over Na2SO4. The solvent was evaporated and the crude residue was purified using 50% ethyl acetate-hexane to give ethyl 2-chloro-3-fluoro-4-methylsulfonyl-benzoate (250 mg, 0.891 mmol) as light yellow solid. 1H NMR (400 MHz, CDCl3) 7.88-7.92 (app. t, 1H), 7.72-7.74 (d, 1H), 4.44 (q, 2H), 3.25 (s, 3H), 1.41 (t, 3H).

Step 4. Preparation of ethyl 3-[tert-butoxycarbonyl (methoxy)amino]-2-chloro-4-methylsulfonyl-benzoate To a flask was added tert-butyl N-methoxycarbamate (629 mg, 1.2 equiv., 4.28 mmol) and N,N-dimethylacetamide (20 mL). At 0° C., potassium tert-butoxide (490 mg, 1.2 equiv., 4.28 mmol) was added in a single portion. The mixture was stirred at 0° C. for five min, then at room temperature for 30 min. Ethyl 2-chloro-3-fluoro-4-methylsulfonyl-benzoate (1 g, 3.56 mmol) was added in a single portion. The reaction mixture was stirred at room temperature for 1 h 45 min.

The reaction mixture was quenched with 10% citric acid, and extracted with diethyl ether. The organic phases were washed with water, dried over MgSO$_4$, filtered and concentrated in vacuo. The material was purified by flash chromatography (0 to 100% EtOAc/hexane) to give ethyl 3-[tert-butoxycarbonyl(methoxy)amino]-2-chloro-4-methylsulfonyl-benzoate (1.12 g, 2.75 mmol) as an orange oil. 1H NMR (400 MHz, chloroform) δ=8.11 (d, J=8.3 Hz, 1H), 7.88 (d, J=8.3 Hz, 1H), 4.53-4.33 (m, 2H), 3.96 (d, J=16.3 Hz, 3H), 3.30-3.14 (m, 3H), 1.60-1.36 (m, 12H)

Step 5. Preparation of ethyl 3-[tert-butoxycarbonyl (methoxy)amino]-2-methyl-4-methylsulfonyl-benzoate To a flask was added ethyl 3-[tert-butoxycarbonyl (methoxy)amino]-2-chloro-4-methylsulfonyl-benzoate (1.78 g, 4.36 mmol), potassium carbonate (2.42 g, 4 equiv., 17.5 mmol) and anhydrous 1,4-dioxane (27 mL). Under a nitrogen atmosphere, was added 2,4,6-trimethyl-1,3,5,2,4,6-trioxatriborinane (1.64 g, 3 equiv., 13.1 mmol) followed by [1,3-bis(2,6-diisopropylphenyl)-2H-imidazol-2-yl]-dichloro-palladium; 3-chloropyridine (297 mg, 0.10 equiv., 0.44 mmol). The reaction mixture was heated at 105° C. for 2 h [the reaction mixture turned black]. The reaction mixture was poured into water and extracted with EtOAc. The organic phase was dried over MgSO$_4$, filtered and concentrated in vacuo. The material was purified by flash chromatography (0 to 40% EtOAc/hexane) to give ethyl 3-[tert-butoxycarbonyl(methoxy)amino]-2-methyl-4-methylsulfonyl-benzoate (1.36 g, 3.51 mmol) as a yellow oil. $^1$H NMR (400 MHz, chloroform) δ=8.04 (d, J=8.3 Hz, 1H), 7.93 (d, J=8.2 Hz, 1H), 4.48-4.32 (m, 2H), 3.89 (br d, J=11.1 Hz, 3H), 3.31-3.14 (m, 3H), 2.61-2.47 (m, 3H), 1.59 (br d, J=0.9 Hz, 5H), 1.47-1.34 (m, 7H)

Step 6. Preparation of ethyl 3-(methoxyamino)-2-methyl-4-methylsulfonyl-benzoate At 0° C., to a flask containing methanol (13.4 mL), was added acetyl chloride (2.5 mL, 10 equiv., 34.6 mmol) and the reaction mixture was stirred for 15 min [to give a 1 M solution of HCl in methanol]. This reaction mixture was added to a flask containing ethyl 3-[tert-butoxycarbonyl (methoxy)amino]-2-chloro-4-methylsulfonyl-benzoate (1.34 g, 3.46 mmol) and the mixture was stirred at room temperature for 2.5 h. The mixture was concentrated in vacuo and the crude material was diluted with dichloromethane and washed with saturated NaHCO$_3$ solution. The organic phase was concentrated in vacuo. The material was purified by flash chromatography (0 to 100% EtOAc/hexane) to give ethyl 3-(methoxyamino)-2-methyl-4-methylsulfonyl-benzoate (477 mg, 1.66 mmol) as a brown oil. 1H NMR (400 MHz, chloroform) δ=8.79 (s, 1H), 7.83 (d, J=8.3 Hz, 1H), 7.66 (d, J=8.3 Hz, 1H), 4.41 (q, J=7.1 Hz, 2H), 3.80 (s, 3H), 3.18 (s, 3H), 2.59 (s, 3H), 1.41 (t, J=7.1 Hz, 3H)

Step 7. Preparation of ethyl 3-[acetyl(methoxy) amino]-2-methyl-4-methylsulfonyl-benzoate To a flask containing sodium hydride (56 mg, 1.2 equiv., 1.46 mmol, 60 mass % in mineral oil) was added anhydrous tetrahydrofuran (10 mL). At 0° C. under a nitrogen atmosphere, was added ethyl 3-(methoxyamino)-2-methyl-4-methylsulfonyl-benzoate (350 mg, 1.22 mmol). The reaction mixture was stirred at room temperature for 20 min. Acetyl chloride (0.1 mL, 1.2 equiv., 1.46 mmol) was added and the reaction mixture was stirred at room temperature for 3 h. The reaction mixture was quenched with saturated NaHCO$_3$ solution and then diluted with dichloromethane. The phases were separated. The organic phase was concentrated in vacuo. The material was purified by flash chromatography (0 to 75% EtOAc/hexane) to give ethyl 3-[acetyl(methoxy) amino]-2-methyl-4-methylsulfonyl-benzoate (236 mg, 0.72 mmol) as an orange oil. $^1$H NMR (400 MHz, chloroform) δ=8.17-8.13 (m, 0.1H), 8.09-8.01 (m, 1H), 7.99-7.92 (m, 0.9H), 4.49-4.37 (m, 2H), 3.90 (s, 0.2H), 3.76 (s, 2.8H), 3.29 (s, 0.2H), 3.14 (s, 2.8H), 2.69 (s, 0.2H), 2.49 (s, 2.8H), 2.39 (s, 2.8H), 1.83 (s, 0.2H), 1.47-1.37 (m, 3H)

Step 8. Preparation of 3-[acetyl(methoxy)amino]-2-methyl-4-methylsulfonyl-benzoic Acid To a stirred solution of ethyl 3-[acetyl(methoxy)amino]-2-methyl-4-methylsulfonyl-benzoate (225 mg, 0.68 mmol) in ethanol (3.9 mL) and water (1.1 mL) was added lithium hydroxide monohydrate (36 mg, 0.86 mmol) and the reaction mixture was stirred at room temperature for 2 h. The reaction mixture was concentrated in vacuo. The reaction mixture was acidified with 2M HCl and extracted with CHCl$_3$/isopropyl alcohol (ratio 7:3). The organic phases were combined, dried over MgSO$_4$, filtered and concentrated in vacuo to give 3-[acetyl(methoxy)amino]-2-methyl-4-methylsulfonyl-benzoic acid (200 mg, 0.66 mmol) as a brown oil. 1H NMR (400 MHz, chloroform) δ=8.13 (d, 1H), 8.08 (d, 1H), 3.78 (s, 3H), 3.16 (s, 3H), 2.56 (s, 3H), 2.41 (s, 3H) Step 9. Preparation of 3-[acetyl(methoxy)amino]-2-methyl-4-methylsulfonyl-N-(1-propyltetrazol-5-yl)benzamide.

To a flask containing 2-chloro-3-[methoxy(methyl) amino]-4-methylsulfonyl-benzoic acid (200 mg, 0.66 mmol) was added anhydrous 1,4-dioxane (6 mL) and the material was heated to 95° C. and N,N'-carbonyldiimidazole (484 mg, 1.5 equiv., 1.00 mmol) was added. The mixture was stirred at 95° C. for 1 h. LCMS analysis showed complete conversion of starting material to the imidazoyl intermediate. The mixture was cooled to room temperature. To a flask was added 2 mL of this reaction mixture, followed by 1,8-diazabicyclo[5.4.0]undec-7-ene (0.03 mL, 1.0 equiv., 0.22 mmol) and 1-propyltetrazol-5-amine (42 mg, 1.5 equiv., 0.33 mmol) and the mixture was stirred at 85° C. overnight. LCMS analysis showed the reaction to be complete. The reaction mixture was concentrated in vacuo. The crude material was diluted with dichloromethane and saturated NaHCO$_3$ solution. Phases were separated. The aqueous layer was extracted with dichloromethane. The aqueous layer was extracted with dichloromethane. The organic phases were combined and dried over MgSO$_4$, filtered and concentrated in vacuo. The material was purified by flash chromatography (0 to 10% MeOH/dichloromethane) to give impure product. The material was purified by preparative HPLC to give 3-[acetyl(methoxy)amino]-2-methyl-4-methylsulfonyl-N-(1-propyltetrazol-5-yl)benzamide (22.7 mg) as a white solid.

PREPARATIVE EXAMPLE 4: PREPARATION OF COMPOUND 1.009

Step 1. Preparation of ethyl 3-[tert-butoxycarbonyl(methoxy)amino]-2-chloro-4-methylsulfonyl-benzoate To a flask was added tert-butyl N-methoxycarbamate (3.15 g, 1.2 equiv., 21.4 mmol) and N,N-dimethylacetamide (100 mL). At 0° C., potassium tert-butoxide (2.45 g, 1.2 equiv., 21.4 mmol) was added in a single portion. The mixture was stirred at 0° C. for five min, then at room temperature for 30 min. Ethyl 2-chloro-3-fluoro-4-methylsulfonyl-benzoate (5 g, 17.8 mmol) was added in a single portion. The reaction mixture was stirred at room temperature for 1 h 15 min. The reaction mixture was quenched with 10% citric acid, and extracted with ether. The organic phases were washed with water, dried over MgSO$_4$, filtered and concentrated in vacuo. The material was purified by flash chromatography (0 to 100% EtOAc/hexane) to give ethyl 3-[tert-butoxycarbonyl(methoxy)amino]-2-chloro-4-methylsulfonyl-benzoate (6.56 g, 16.1 mmol) as an orange oil. 1H NMR (400 MHz, chloroform) δ=8.11 (d, J=8.3 Hz, 1H), 7.88 (d, J=8.3 Hz, 1H), 4.53-4.33 (m, 2H), 3.96 (d, J=16.3 Hz, 3H), 3.30-3.14 (m, 3H), 1.60-1.36 (m, 12H)

Step 2. Preparation of ethyl 2-chloro-3-(methoxyamino)-4-methylsulfonyl-benzoate To a flask containing ethyl 3-[tert-butoxycarbonyl(methoxy)amino]-2-chloro-4-methylsulfonyl-benzoate (3.46 g, 8.48 mmol), was added dichloromethane (28 mL) and trifluoroacetic acid (6.9 mL). The mixture was stirred at room temperature for 1.5 h. The mixture was concentrated in vacuo and the crude material was diluted with dichloromethane and washed with water. The organic phase was concentrated in vacuo. The material was purified by flash chromatography (100% dichloromethane) to give ethyl 2-chloro-3-(methoxyamino)-4-methylsulfonyl-benzoate (1 g, 3.25 mmol) as a yellow oil. $^1$H NMR (400 MHz, chloroform) δ=8.57 (s, 1H), 7.94 (d, J=8.3 Hz, 1H), 7.56 (d, J=8.3 Hz, 1H), 4.44 (q, J=7.1 Hz, 2H), 3.90 (s, 3H), 3.23 (s, 3H), 1.42 (t, J=7.2 Hz, 3H)

Step 3. Preparation of ethyl 3-[acetyl(methoxy)amino]-2-chloro-4-methylsulfonyl-benzoate To a flask containing sodium hydride (60 mg, 1.2 equiv., 1.56 mmol, 60 mass %) was added anhydrous tetrahydrofuran (10 mL). At 0° C. under a nitrogen atmosphere, was added ethyl 3-(methoxyamino)-2-methyl-4-methylsulfonyl-benzoate (400 mg, 1.30 mmol). The reaction mixture was stirred at room temperature for 20 min. Acetyl chloride (0.11 mL, 1.2 equiv., 1.56 mmol) was added and the reaction mixture was stirred at room temperature overnight. The reaction mixture was quenched with saturated NaHCO$_3$ solution and then diluted with dichloromethane. The phases were separated. The organic phase was concentrated in vacuo. The material was purified by flash chromatography (0 to 100% EtOAc/hexane) to give ethyl 3-[acetyl(methoxy)amino]-2-chloro-4-methylsulfonyl-benzoate (352 mg, 1.01 mmol) as a yellow oil. $^1$H NMR (400 MHz, chloroform) δ=8.21 (d, J=8.2 Hz, 0.1H), 8.12 (d, J=8.3 Hz, 0.9H), 7.98 (d, J=8.2 Hz, 0.1H), 7.91 (d, J=8.3 Hz, 0.9H), 4.52-4.40 (m, 2H), 3.98 (s, 0.4H), 3.85 (s, 2.6H), 3.32 (s, 0.4H), 3.15 (s, 2.6H), 2.41 (s, 2.6H), 1.90 (s, 0.4H), 1.49-1.38 (m, 3H)

Step 4. Preparation of 3-[acetyl(methoxy)amino]-2-chloro-4-methylsulfonyl-benzoic Acid To a stirred solution of ethyl 3-[acetyl(methoxy)amino]-2-chloro-4-methylsulfonyl-benzoate (330 mg, 0.94 mmol) in ethanol (5.4 mL) and water (1.5 mL) was added lithium hydroxide monohydrate (99 mg, 2.36 mmol) and the reaction mixture was stirred at room temperature for 2 h. The reaction mixture was concentrated in vacuo to remove ethanol. The reaction mixture was acidified with 2M HCl and then extracted with CHCl$_3$/isopropyl alcohol (ratio 7:3) and the organic phase was combined, dried over MgSO$_4$, filtered and concentrated in vacuo to give 3-[acetyl(methoxy)amino]-2-chloro-4-methylsulfonyl-benzoic acid (275 mg, 0.85 mmol) as a yellow oil. 1H NMR (400 MHz, chloroform) δ=8.19-8.11 (m, 1H), 8.04 (d, J=8.3 Hz, 1H), 3.86 (s, 3H), 3.17 (s, 3H), 2.43 (s, 3H)

Step 5. Preparation of 3-[acetyl(methoxy)amino]-2-chloro-4-methylsulfonyl-N-(1-propyltetrazol-5-yl)benzamide To a flask containing 3-[acetyl(methoxy)amino]-2-chloro-4-methylsulfonyl-benzoic acid (260 mg, 0.81 mmol) was added anhydrous 1,4-dioxane (6 mL) and the material was heated to 100° C. and N,N'-carbonyldiimidazole (197 mg, 1.5 equiv., 1.00 mmol) was added. The mixture was stirred at 100° C. for 2 h. LCMS analysis showed complete conversion of starting material to the imidazoyl intermediate. The mixture was cooled to room temperature. To a flask was added 2 mL of this reaction mixture, followed by 1,8-diazabicyclo[5.4.0]undec-7-ene (0.12 mL, 1.0 equiv., 0.22 mmol) and 1-propyltetrazol-5-amine (154 mg, 1.5 equiv., 0.33 mmol) and the mixture was stirred at 100° C. overnight. LCMS analysis showed the reaction to be complete. The reaction mixture was concentrated in vacuo. The crude material was diluted with dichloromethane and saturated NaHCO$_3$ solution. Phases were separated. The aqueous layer was extracted with dichloromethane. The organic phases were combined and dried over MgSO$_4$, filtered and concentrated in vacuo. The material was purified by flash chromatography (0 to 10% MeOH/dichloromethane) to give 3-[acetyl(methoxy)amino]-2-chloro-4-methylsulfonyl-N-(1-propyltetrazol-5-yl)benzamide (E, 50.1 mg, 0.12 mmol) as a white solid.

PREPARATIVE EXAMPLE 5: PREPARATION OF COMPOUND 1.043

Step 1. Preparation of ethyl 2-chloro-3-(methoxyamino)-4-methylsulfonyl-benzoate Acetyl chloride (3.88 mL, 54.0 mmol) was added dropwise to MeOH (22 mL, 542 mmol) (ice/water bath) and the solution was then stirred at RT for 15 min (to generate a 1 M solution of HCl in methanol). This solution was added to a solution ethyl 3-[tert-butoxycarbonyl(methoxy)amino]-2-chloro-4-methylsulfonyl-benzoate (2.206 g, 5.408 mmol) in MeOH (5 mL) at 0° C. and the reaction mixture was then stirred for at RT for 2 hours. The solvent was reduced in volume and the residue was dissolved in DCM and was then washed with aq NaHCO₃. The organic layer was evaporated to give ethyl 2-chloro-3-(methoxyamino)-4-methylsulfonyl-benzoate (1.48 g, 4.81 mmol) as a yellow oil. 1H NMR (CDCl₃): 8.58 (broad s, 1H), 7.95 (d, 1H), 7.56 (d, 1H), 4.45 (q, 2H), 3.90 (s, 3H), 3.24 (s, 3H), 1.42 (t, 3H).

Step 2. Preparation of ethyl 2-chloro-3-[methoxy(methyl)amino]-4-methylsulfonyl-benzoate n-BuLi (1.6M in hexanes) (3.3 mL, 5.3 mmol) was added dropwise (over 20 mins) (maintaining temp below −70° C.) to a solution of ethyl 2-chloro-3-(methoxyamino)-4-methylsulfonyl-benzoate (1.48 g, 4.81 mmol) in THF (22 mL) under N₂, dry ice/acetone bath. The reaction mixture was stirred at this temp for 20 min and then dimethyl sulphate (1.38 mL, 14.4 mmol) was added in one portion (again keeping temp below −70° C.). The RM was stirred at −78° C. for 1.5 h. The reaction mixture was then allowed to warm to 0° C. over 30 min and was stirred at this temperature for a further 1 h. The reaction mixture was quenched with sodium metabisulphite and the mixture was extracted with EtOAc, and the organic phase was dried (MgSO₄), filtered and concentrated to produce a yellow oil. Flash chromatography (0-100% EtOAc/isohexane over 25 min) gave ethyl 2-chloro-3-[methoxy(methyl)amino]-4-methylsulfonyl-benzoate (1.33 g, 4.14 mmol) as a yellow oil. 1H NMR (CDCl₃): 8.07 (d, 1H), 7.58 (d, 1H), 4.45 (q, 2H), 3.66 (s, 3H), 3.40 (s, 3H), 3.29 (s, 3H), 1.42 (t, 3H).

Step 3. Preparation of 2-chloro-3-[methoxy(methyl)amino]-4-methylsulfonyl-benzoic Acid Lithium; hydroxide hydrate (169 mg, 4.028 mmol) in water (5 mL) was added dropwise to a stirred solution of ethyl 2-chloro-3-[methoxy(methyl)amino]-4-methylsulfonyl-benzoate (1.17 g, 3.65 mmol) in EtOH (20 mL). The reaction mixture was stirred at RT for 1.5 h and then concentrated to remove the ethanol. The residue was dissolved in water and was washed with DCM. The basic aqueous phase was acidified (aq citric acid) and was extracted with DCM, dried (MgSO₄) and concentrated under reduced pressure to give 2-chloro-3-[methoxy(methyl)amino]-4-methylsulfonyl-benzoic acid as a white solid (876 mg, 2.98 mmol). 1H NMR (CDCl₃): 8.12 (d, 1H), 7.78 (d, 1H), 3.67 (s, 3H), 3.42 (s, 1H), 3.31 (s, 3H).

Step 4. Preparation of 2-chloro-3-[methoxy(methyl)amino]-4-methylsulfonyl-N-(1-methyltetrazol-5-yl)benzamide 2-chloro-3-[methoxy(methyl)amino]-4-methylsulfonyl-benzoic acid (876 mg, 2.98 mmol) in 1,4-dioxane (25 mL) was heated to 100° C. and then N,N'-carbonyldiimidazole (741 mg, 4.57 mmol) was added (in one portion, effervescence observed). The reaction mixture was heated at 100° C. for 1 h and was then cooled to 85° C. 1-Methyltetrazol-5-amine (443 mg, 4.47 mmol) followed by DBU (0.45 mL, 2.9 mmol) were added and the reaction mixture was heated at 85° C. for 16 h. The reaction mixture was cooled to RT and evaporated to remove solvent and water was added to the residue. The mixture was washed with EtOAc and then acidified with dilute HCl solution. It was then extracted with EtOAc. This extraction was concentrated under reduced pressure to give a pink foam. Chromatography (0 to 5% MeOH in CH₂Cl₂) gave a yellow foam that was triturated with isoxhexane/diethyl either to provide 2-chloro-3-[methoxy(methyl)amino]-4-methylsulfonyl-N-(1-methyltetrazol-5-yl)benzamide (489 mg, 1.30 mmol) as a pale yellow powder. 1H NMR (CDCl₃): 10.77 (broad s, 1H), 8.15 (d, 1H), 7.62 (d, 1H), 4.16 (s, 3H), 3.67 (s, 3H), 3.45 (s, 3H), 3.30 (s, 3H).

TABLE 1

Examples of herbicidal compounds of the present invention.

| Compound Number | R¹ | R² | R³ | R⁴ | R⁵ | 1H-NMR |
|---|---|---|---|---|---|---|
| 1.001 | Me | Cl | CF₃ | —C(O)CH₃ | —CH₃ | 1HNMR(400 MHz, chloroform) 11.11(brs, 1H), 7.96-7.59(m, 2H), 4.16-4.01(m, 3H), 3.89-3.76(m, 3H), 2.34-1.85(m, 3H) |
| 1.002 | Et | Cl | CF₃ | —C(O)CH₃ | —CH₃ | 1H NMR (400 MHz, CDCl3) δ = 7.89-7.63 (m, 2H), 4.55-4.31 (m, 2H), 3.78 (s, 3H), 2.36 (s, 3H), 1.60 (m, 3H) |
| 1.003 | n-Pr | Cl | CF₃ | —C(O)CH₃ | —CH₃ | |
| 1.004 | Me | —CH₃ | CF₃ | —C(O)CH₃ | —CH₃ | 1H NMR (400 MHz, DMSO) δ 11.84 (br, s, 1H), 7.86-7.95 (m, 2H), 4.01 (s, 3H), 3.70 (s, 3H), 2.30-2.31 (6H). |
| 1.005 | Et | —CH₃ | CF₃ | —C(O)CH₃ | —CH₃ | |
| 1.006 | n-Pr | —CH₃ | CF₃ | —C(O)CH₃ | —CH₃ | |
| 1.007 | Me | Cl | —S(O)₂Me | —C(O)CH₃ | —CH₃ | 1H NMR (400 MHz, chloroform) δ = 8.17 (d, J = 8.2 Hz, 1H), 7.85 (d, J = 8.2 Hz, 1H), 4.10 (s, 3H), 3.86 (s, 3H), 3.19 (s, 3H), 2.38 (s, 3H) |
| 1.008 | Et | Cl | —S(O)₂Me | —C(O)CH₃ | —CH₃ | 1H NMR (400 MHz, chloroform) δ = 8.29-8.09 (m, 1H), 7.85 (d, J = 8.2 Hz, 1H), 4.45 (q, J = 7.3 Hz, 2H), 3.86 (s, 3H), 3.19 (s, 3H), 2.38 (s, 3H), 1.68-1.56 (m, 3H) |

TABLE 1-continued

Examples of herbicidal compounds of the present invention.

| Compound Number | R¹ | R² | R³ | R⁴ | R⁵ | 1H-NMR |
|---|---|---|---|---|---|---|
| 1.009 | n-Pr | Cl | —S(O)₂Me | —C(O)CH₃ | —CH₃ | 1H NMR (400 MHz, chloroform) $\delta$ = 8.24 (d, J = 8.1Hz, 1H), 7.84 (d, J = 8.1 Hz, 1H), 4.43-4.19 (m, 2H), 3.86 (s, 3H), 3.19 (s, 3H), 2.43-2.28 (m, 3H), 2.09-1.95 (m, 2H), 1.04-0.92 (m, 3H) |
| 1.010 | Me | —CH₃ | —S(O)₂Me | —C(O)CH₃ | —CH₃ | 1H NMR (400 MHz, chloroform) $\delta$ = 10.95-10.10 (m, 1H), 8.01 (d, J = 8.2 Hz, 1H), 7.81 (d, J = 8.2 Hz, 1H), 4.09 (s, 3H), 3.77 (s, 3H), 3.17 (s, 3H), 2.43 (s, 3H), 2.33 (s, 3H) |
| 1.011 | Et | —CH₃ | —S(O)₂Me | —C(O)CH₃ | —CH₃ | 1H NMR (400 MHz, chloroform) $\delta$ = 10.77-10.34 (m, 1H), 8.01 (d, J = 8.1 Hz, 1H), 7.82 (d, J = 8.2 Hz, 1H), 4.43 (q, J = 7.2 Hz, 2H), 3.77 (s, 3H), 3.17 (s, 3H), 2.44 (s, 3H), 2.33 (s, 3H), 1.62 (t, J = 7.3 Hz, 3H) |
| 1.012 | n-Pr | —CH₃ | —S(O)₂Me | —C(O)CH₃ | —CH₃ | 1H NMR (400 MHz, chloroform, rotamers) $\delta$ = 8.13 (d, J = 8.4 Hz, 0.05H), 7.99 (d, J = 8.1 Hz, 0.95H), 7.96 (br s, 0.05H), 7.79 (d, J = 8.2 Hz, 0.95H), 4.41-4.31 (m, 2H), 3.87 (s, 0.2H), 3.77 (s, 2.8H), 3.28 (s, 0.2H), 3.17 (s, 2.8H), 2.61 (s, 0.2H), 2.42 (s, 2.8H), 2.33 (s, 2.8H), 2.09-1.95 (m, 2H), 1.83 (s, 0.2H), 1.05-0.91 (m, 3H) |
| 1.013 | Me | Cl | CF₃ | —C(O)OC₂H₅ | —CH₃ | |
| 1.014 | Et | Cl | CF₃ | —C(O)OC₂H₅ | —CH₃ | |
| 1.015 | n-Pr | Cl | CF₃ | —C(O)OC₂H₅ | —CH₃ | |
| 1.016 | Me | —CH₃ | CF₃ | —C(O)OC₂H₅ | —CH₃ | |
| 1.017 | Et | —CH₃ | CF₃ | —C(O)OC₂H₅ | —CH₃ | |
| 1.018 | n-Pr | —CH₃ | CF₃ | —C(O)OC₂H₅ | —CH₃ | |
| 1.019 | Me | Cl | —S(O)₂Me | —C(O)OC₂H₅ | —CH₃ | 1H NMR (400 MHz, chloroform, rotamers) $\delta$ = 8.24-8.15 (m, 0.4H), 8.10 (br d, J = 8.2 Hz, 0.6H), 7.93-7.75 (m, 1H), 4.40-4.17 (m, 2H), 4.14-4.02 (m, 3H), 3.98 (s, 1.1H), 3.92 (s, 1.9H), 3.28 (s, 1.1H), 3.23 (s, 1.9H), 1.40 (br t, J = 7.0 Hz, 1.9H), 1.18 (br t, J = 6.9 Hz, 1.1H) |
| 1.020 | Et | Cl | —S(O)₂Me | —C(O)OC₂H₅ | —CH₃ | 1H NMR (400 MHz, chloroform, rotamers) $\delta$ = 8.18 (br d, J = 7.2 Hz, 0.4H), 8.09 (br d, J = 7.8 Hz, 0.6H), 7.94-7.76 (m, 1H), 4.44 (br s, 2H), 4.36-4.15 (m, 2H), 3.98 (s, 1.1H), 3.92 (s, 1.9H), 3.28 (s, 1.1H), 3.22 (s, 1.9H), 1.60 (br d, J = 6.1 Hz, 3H), 1.40 (br s, 1.9H), 1.17 (br s, 1.1H) |
| 1.021 | n-Pr | Cl | —S(O)₂Me | —C(O)OC₂H₅ | —CH₃ | |
| 1.022 | Me | —CH₃ | —S(O)₂Me | —C(O)OC₂H₅ | —CH₃ | |
| 1.023 | Et | —CH₃ | —S(O)₂Me | —C(O)OC₂H₅ | —CH₃ | |
| 1.024 | n-Pr | —CH₃ | —S(O)₂Me | —C(O)OC₂H₅ | —CH₃ | |
| 1.025 | Me | Cl | CF₃ | —C(O)OC(CH₃)₃ | —CH₃ | 1HNMR(400 MHz, chloroform, rotameric)7.83(brd, J = 10.1 Hz, 2H), 4.14(brs, 3H), 3.94-3.78(m, 3H), 1.64-1.29(m, 9H) |
| 1.026 | Et | Cl | CF₃ | —C(O)OC(CH₃)₃ | —CH₃ | |
| 1.027 | n-Pr | Cl | CF₃ | —C(O)OC(CH₃)₃ | —CH₃ | |
| 1.028 | Me | —CH₃ | CF₃ | —C(O)OC(CH₃)₃ | —CH₃ | |
| 1.029 | Et | —CH₃ | CF₃ | —C(O)OC(CH₃)₃ | —CH₃ | |
| 1.030 | n-Pr | —CH₃ | CF₃ | —C(O)OC(CH₃)₃ | —CH₃ | |
| 1.031 | Me | Cl | —S(O)₂Me | —C(O)OC(CH₃)₃ | —CH₃ | 1H NMR (400 MHz, chloroform, rotamers) $\delta$ = 8.17 (d, J = 8.4 Hz, 0.4H), 8.11 (d, J = 7.8 Hz, 0.6H), 7.90-7.77 (m, 1H), 4.12-4.09 (m, 3H), 3.95 (s, 1.2H), 3.90 (s, 1.8H), 3.28 (s, 1.2H), 3.22 (s, 1.8H), 1.55 (s, 5.3H), 1.37 (s, 3.7H) |

TABLE 1-continued

Examples of herbicidal compounds of the present invention.

| Compound Number | R$^1$ | R$^2$ | R$^3$ | R$^4$ | R$^5$ | 1H-NMR |
|---|---|---|---|---|---|---|
| 1.032 | Et | Cl | —S(O)$_2$Me | —C(O)OC(CH$_3$)$_3$ | —CH$_3$ | |
| 1.033 | n-Pr | Cl | —S(O)$_2$Me | —C(O)OC(CH$_3$)$_3$ | —CH$_3$ | |
| 1.034 | Me | —CH$_3$ | —S(O)$_2$Me | —C(O)OC(CH$_3$)$_3$ | —CH$_3$ | |
| 1.035 | Et | —CH$_3$ | —S(O)$_2$Me | —C(O)OC(CH$_3$)$_3$ | —CH$_3$ | |
| 1.036 | n-Pr | —CH$_3$ | —S(O)$_2$Me | —C(O)OC(CH$_3$)$_3$ | —CH$_3$ | |
| 1.037 | Me | C | CF | —CH$_3$ | —CH$_3$ | 1HNMR(400 MHz, chloroform) 10.64(brs, 1H),7.73(d, J = 8.2 Hz, 1H), 7.60(d, J = 8.1 Hz, 1H), 4.15(s, 3H), 3.57(s, 3H),3.19(s, 3H) |
| 1.038 | Et | Cl | CF$_3$ | —CH$_3$ | —CH$_3$ | |
| 1.039 | n-Pr | Cl | CF$_3$ | —CH$_3$ | —CH$_3$ | |
| 1.040 | Me | —CH$_3$ | CF$_3$ | —CH$_3$ | —CH$_3$ | |
| 1.041 | Et | —CH$_3$ | CF$_3$ | —CH$_3$ | —CH$_3$ | |
| 1.042 | n-Pr | —CH$_3$ | CF$_3$ | —CH$_3$ | —CH$_3$ | |
| 1.043 | Me | Cl | —S(O)$_2$Me | —CH$_3$ | —CH$_3$ | 1H NMR (400 MHz, chloroform) δ = 10.77 (br s, 1H), 8.15 (d, J = 8.2 Hz, 1H), 7.62 (d, J = 8.3 Hz, 1H), 4.16 (s, 3H), 3.67 (s, 3H), 3.45 (s, 3H), 3.30 (s, 3H) |
| 1.044 | Et | Cl | —S(O)$_2$Me | —CH$_3$ | —CH$_3$ | 1H NMR (400 MHz, chloroform) δ = 10.83 (br s, 1H), 8.14 (d, J = 8.2 Hz, 1H), 7.60 (d, J = 8.2 Hz, 1H), 4.52 (q, J = 7.3 Hz, 2H), 3.66 (s, 3H), 3.44 (s, 3H), 3.29 (s, 3H), 1.63 (t, J = 7.3 Hz, 3H) |
| 1.045 | n-Pr | Cl | —S(O)$_2$Me | —CH$_3$ | —CH$_3$ | 1H NMR (400 MHz, chloroform) δ = 11.10-10.75 (m, 1H), 8.13 (d, J = 8.2 Hz, 1H), 7.59 (d, J = 8.2 Hz, 1H), 4.45 (t, J = 7.4 Hz, 2H), 3.66 (s, 3H), 3.44 (s, 3H), 3.29 (s, 3H), 2.03 (sxt, J = 7.4 Hz, 2H), 0.99 (t, J = 7.4 Hz, 3H) |
| 1.046 | Me | —CH$_3$ | —S(O)$_2$Me | —CH$_3$ | —CH$_3$ | |
| 1.047 | Et | —CH$_3$ | —S(O)$_2$Me | —CH$_3$ | —CH$_3$ | |
| 1.048 | n-Pr | —CH$_3$ | —S(O)$_2$Me | —CH$_3$ | —CH$_3$ | |
| 1.049 | Me | Cl | CF$_3$ | —C(O)iPr | —CH$_3$ | 1H NMR (400 MHz, CDCl3) δ = 10.63-9.40 (m, 1H), 7.26 (s, 2H), 4.31-3.52 (m, 6H), 3.43-2.97 (m, 1H), 1.41-1.01 (m, 6H) |
| 1.050 | Me | Cl | CF$_3$ | —C(O)C$_2$H$_5$ | —CH$_3$ | 1H NMR (400 MHz, CDCl3) δ = 7.93-7.63 (m, 2H), 4.16-3.64 (m, 6H), 2.69 (d, 2H), 1.15 (t, 3H) |
| 1.051 | Me | Cl | CF$_3$ | —C(O)CH$_2$CH(CH$_3$)$_2$ | —CH$_3$ | 1H NMR (400 MHz, CDCl3) δ = 7.92-7.79 (m, 2H), 4.10 (s, 3H), 3.75 (s, 3H), 2.55 (br d, 2H), 2.32-1.98 (m, 1H), 1.02 (m, 6H) |
| 1.052 | Me | Cl | CF$_3$ | —C(O)CH$_3$ | —C$_2$H$_5$ | 1H NMR (400 MHz, CDCl3) δ = 7.76 (d, 2H), 4.07 (m, 5H), 2.33 (s, 3H), 1.24 (t, 3H) |
| 1.053 | Me | Cl | CF$_3$ | —CH$_3$ | —C$_2$H$_5$ | 1H NMR (400 MHz, DMSO-d6) δ ppm 11.96 (br s, 1H) 7.74-7.91 (m, 2 H) 4.02 (s, 3H) 3.62-3.76 (m, 2 H) 3.11 (s, 3H) 1.11 (t, 3H). |
| 1.054 | Me | Cl | —S(O)$_2$nPr | —CH$_3$ | —CH$_3$ | 1H NMR (400 MHz, CHLOROFORM-d) δ ppm 8.05-8.16 (d, J = 8.1 Hz, 1H) 7.56-7.67 (d, J = 8.1 Hz, 1H) 4.55 (br d, J = 6.48 Hz, 2 H) 3.56-3.72 (m, 5H) 3.29 (s, 3H) 1.66-1.92 (m, 2 H) 1.55-1.64 (m, 3H) 1.02-1.15 (m, 3H) |
| 1.055 | Et | Cl | —S(O)$_2$Me | —CH$_3$ | —C$_2$H$_5$ | 1H NMR (400 MHz, DMSO-d6) δ ppm 11.89 (br s, 1H) 8.04 (d, J = 8.03 Hz, 1H) 7.82 (d, J = 8.03 Hz, 1H) 4.37 (q, J = 7.28 Hz, 2 H) 3.86 (q, 2H) 3.53 (s, 3H) 3.20 (s, 3H) 1.47 (t, J = 7.28 Hz, 3H) 1.13 (t, J = 7.3, 3H) |
| 1.056 | Me | Cl | —S(O)$_2$Me | —CH$_3$ | -nPr | 1H NMR (400 MHz, DMSO-d6) δ ppm 11.98 (br s, 1H) 8.05 (d, J = 8.19 Hz, 1H) 7.84 (d, J = 7.95 Hz, 1H) 4.01 (s, 3H) 3.77 (br s, 2 H) 3.53 (s, 3H) 3.20 (s, 3H) 1.47-1.58 (m, 2 H) 0.86 (t, J = 7.40 Hz, 3H) |

TABLE 1-continued

Examples of herbicidal compounds of the present invention.

| Compound Number | R¹ | R² | R³ | R⁴ | R⁵ | 1H-NMR |
|---|---|---|---|---|---|---|
| 1.057 | Me | Cl | —S(O)₂Me | —CH₃ | -iPr | 1H NMR (400 MHz, CHLOROFORM-d) δ ppm 10.83-11.08 (br s, 1H) 8.12 (d, J = 8.1 Hz, 1H) 7.57 (d, J = 8.1 Hz, 1H) 4.15 (s, 3H) 4.06-4.13 (m, 1H) 3.42 (s, 3H) 3.26 (s, 3H) 1.25-1.28 (m, 3H) 1.11-1.13 (m, 3H) |
| 1.058 | Me | Cl | —S(O)₂Me | —C₂H₅ | —C₂H₅ | 1H NMR (400 MHz, DMSO-d6) δ ppm 11.4 (br s, 1H) 8.07 (d, J = 8.07 Hz, 1H) 7.72 (d, J = 8.19 Hz, 1H) 4.01 (s, 3H) 3.86 (q, J = 6.97 Hz, 2 H) 3.39-3.54 (m, 5H) 1.28-1.31 (m, 3H) 1.12-1.15 (m, 3H) |
| 1.059 | Me | Cl | —S(O)₂Me | —C(O)CH₃ | —C₂H₅ | 1H NMR (400 MHz, DMSO-d6) δ ppm 12.13 (br s, 1H) 8.18 (d, J = 8 Hz 1H) 8.09 (d, J = 8.1 Hz, 1H) 4.06 (q, 2 H) 4.01 (s, 3H) 3.30 (s, 3H) 2.27 (s, 3H) 1.18-1.23 (m, 3H) |
| 1.060 | Me | Cl | —S(O)₂Me | —CH₃ | —C₂H₅ | 1H NMR (400 MHz, DMSO-d6) δ ppm 11.98 (br s, 1H) 8.04 (d, J = 8.19 Hz, 1H) 7.83 (d, J = 8.07 Hz, 1H) 4.01 (s, 3H) 3.79-3.92 (q, 2H) 3.53 (s, 3H) 3.20 (s, 3H) 1.13 (t, J = 6.97 Hz, 3H) |
| 1.061 | Me | Cl | —S(O)₂nPr | —CH₃ | —CH₃ | 1H NMR (400 MHz, CHLOROFORM-d) δ ppm 10.49-11.41 (br s, 1H) 8.09 (d, J = 7.46 Hz, 1H) 7.60-7.62 (d, J = 8 Hz, 1H) 4.16 (s, 3H) 3.54-3.67(m, 5H) 3.28 (s, 3H) 1.71-1.89 (m, 2 H) 1.00-1.14 (m, 3H) |
| 1.062 | Me | Cl | —S(O)₂Et | —CH₃ | —CH₃ | 1H NMR (400 MHz, CHLOROFORM-d) δ ppm 11.11 (br s, 1H) 8.10 (d, J = 8.07 Hz, 1H) 7.60 (d, J = 8.07 Hz, 1H) 4.15 (s, 3H) 3.62-3.66 (m, 5H) 3.28 (s, H) 1.35 (t, J = 7.46 Hz, 3H) |
| 1.063 | Me | F | —CF₃ | —C(O)C(CH₃)₃ | —CH₃ | 1H NMR (400 MHz, DMSO δ 11.96 (brs, 1H), 8.10 (t, 1H), 7.89 (d, 1H), 3.99 (s, 3H), 3.75 (s, 3H), 1.41 (s, 9H). |
| 1.064 | Me | F | —CF₃ | —C(O)CH₃ | —CH₃ | 1H NMR (400 MHz, DMSO) δ 11.99 (brs, 1H), 8.13 (t, 1H), 7.92 (d, 1H), 3.96 (s, 3H), 3.76 (s, 3H), 2.32 (s, 3H). |
| 1.065 | Me | F | —CF₃ | —CH₃ | —CH₃ | 1H NMR (400 MHz, DMSO ) δ 11.88 (brs, 1H), 7.90 (t, 1H), 7.73 (d, 1H), 3.99 (s, 3H), 3.50 (s, 3H), 3.06 (s, 3H). |
| 1.066 | Et | Cl | —S(O)₂Me | —CH₃ | -iPr | |
| 1.067 | Me | Cl | —S(O)₂Me | —CH₃ | CF₃CH₂ | |
| 1.068 | Me | Cl | —CF₃ | —C(O)nPr | —CH₃ | |
| 1.069 | Me | Cl | —S(O)₂Me | —C(O)iPr | —CH₃ | |
| 1.070 | Me | Cl | —CF₃ | —C₂H₅ | —C₂H₅ | |
| 1.071 | Me | Cl | —CF₃ | —CH₃ | nPr | |
| 1.072 | Me | Cl | —CF₃ | nPr | —CH₃ | |
| 1.073 | Me | Cl | —CHF₂ | —C(O)CH₃ | —CH₃ | |
| 1.074 | Me | Cl | —CHF₂ | —CH₃ | —CH₃ | |
| 1.075 | Et | Cl | —CHF₂ | —C(O)CH₃ | —CH₃ | |
| 1.076 | n-Pr | Cl | —CHF₂ | —C(O)CH₃ | —CH₃ | |
| 1.077 | Me | —CH₃ | —CHF₂ | —C(O)CH₃ | —CH₃ | |
| 1.078 | Me | Cl | —CHF₂ | —C(O)OC(CH₃)₃ | —CH₃ | |
| 1.079 | Me | Cl | —CHF₂ | —C(O)iPr | —CH₃ | |
| 1.080 | Me | Cl | —CHF₂ | —C(O)C₂H₅ | —CH₃ | |
| 1.081 | Me | Cl | —CHF₂ | —C(O)CH₂CH(CH₃)₂ | —CH₃ | |
| 1.082 | Me | Cl | —CHF₂ | —C(O)CH₃ | —C₂H₅ | |
| 1.083 | Me | Cl | —CHF₂ | —CH₃ | —C₂H₅ | |
| 1.084 | Me | F | —CHF₂ | —C(O)C(CH₃)₃ | —CH₃ | |
| 1.085 | Me | F | —CHF₂ | —C(O)CH₃ | —CH₃ | |
| 1.086 | Me | F | —CHF₂ | —CH₃ | —CH₃ | |
| 1.087 | Me | Cl | —CHF₂ | —C(O)nPr | —CH₃ | |

TABLE 1-continued

Examples of herbicidal compounds of the present invention.

| Compound Number | R¹ | R² | R³ | R⁴ | R⁵ | 1H-NMR |
|---|---|---|---|---|---|---|
| 1.088 | Me | Cl | —CHF₂ | —C₂H₅ | —C₂H₅ | |
| 1.089 | Me | Cl | —CHF₂ | —CH₃ | nPr | |
| 1.090 | Me | Cl | —CHF₂ | nPr | —CH₃ | |

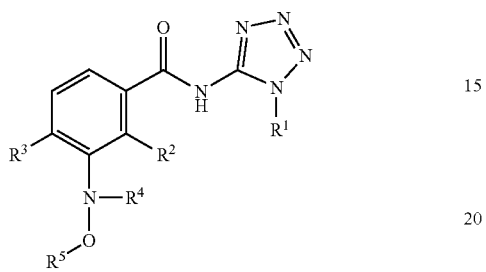

TABLE 2

Examples of herbicidal compounds of the present invention.

| Compound Number | R¹ | R² | R³ | R⁴ | R⁵ | 1H-NMR |
|---|---|---|---|---|---|---|
| 2.001 | —CH₃ | Cl | CF₃ | —C(O)CH₃ | —CH₃ | 1H NMR (400 MHz, chloroform, rotameric) δ = 7.90-7.64 (m, 2H), 3.91 (s, 0.4H), 3.76 (s, 2.6H), 2.53 (s, 3H), 2.35 (s, 2.6H), 1.85 |
| 2.002 | —CH₃ | —CH₃ | CF₃ | —C(O)CH₃ | —CH₃ | 1H NMR (400 MHz, DMSO) δ 12.25 (br, s, 1H), 7.77-7.83 (m, 2H), 3.69 (s, 3H), 2.48 (s, 3H), 2.29 (s, 3H), 2.26 (s, 3H). |
| 2.003 | —CH₃ | Cl | —S(O)₂Me | —C(O)CH₃ | —CH₃ | |
| 2.004 | —CH₃ | —CH₃ | —S(O)₂Me | —C(O)CH₃ | —CH₃ | |
| 2.005 | —CH₃ | Cl | CF₃ | —C(O)OC₂H₅ | —CH₃ | |
| 2.006 | —CH₃ | —CH₃ | CF₃ | —C(O)OC₂H₅ | —CH₃ | |
| 2.007 | —CH₃ | Cl | —S(O)₂Me | —C(O)OC₂H₅ | —CH₃ | |
| 2.008 | —CH₃ | —CH₃ | —S(O)₂Me | —C(O)OC₂H₅ | —CH₃ | |
| 2.009 | —CH₃ | Cl | CF3 | —C(O)OC(CH₃)₃ | —CH₃ | 1HNMR(400 MHz, chloroform, rotameric) 7.84(brd, J = 8.2 Hz, 1H), 7.71(d, J = 8.3 Hz, 1H), 3.92-3.75(m, 3H), 2.55(s, 3H), 1.64-1.31(m, 9H) |
| 2.010 | —CH₃ | —CH₃ | CF₃ | —C(O)OC(CH₃)₃ | —CH₃ | |
| 2.011 | —CH₃ | Cl | —S(O)₂Me | —C(O)OC(CH₃)₃ | —CH₃ | |
| 2.012 | —CH₃ | —CH₃ | —S(O)₂Me | —C(O)OC(CH₃)₃ | —CH₃ | |
| 2.013 | —CH₃ | Cl | CF₃ | —CH₃ | —CH₃ | |
| 2.014 | —CH₃ | —CH₃ | CF₃ | —CH₃ | —CH₃ | |
| 2.015 | —CH₃ | Cl | —S(O)₂Me | —CH₃ | —CH₃ | |
| 2.016 | —CH₃ | —CH₃ | —S(O)₂Me | —CH₃ | —CH₃ | |
| 2.017 | Me | Cl | CF₃ | —C(O)iPr | —CH₃ | |
| 2.018 | Me | Cl | CF₃ | —C(O)C₂H₅ | —CH₃ | 1H NMR (400 MHz, CDCl3) δ = 7.73 (s, 3H), 7.61-7.29 (m, 1H), 3.75 (s, 3H), 2.70 (d, 2H), 2.54 (s, 3H), 1.16 (t, 3H) |
| 2.019 | Me | Cl | CF₃ | —C(O)CH₂CH(CH₃)₂ | —CH₃ | 1H NMR (500 MHz, CDCl3) δ = 7.75-7.63 (m, 1H), 7.68 (d, 1H), 3.72 (s, 3H), 2.58-2.45 (m, 5H), 2.19 (s, 1H), 1.01 (dd, 6H) |

TABLE 2-continued

Examples of herbicidal compounds of the present invention.

| Compound Number | R¹ | R² | R³ | R⁴ | R⁵ | 1H-NMR |
|---|---|---|---|---|---|---|
| 2.020 | Me | Cl | CF₃ | —C(O)C₂H₅ | —CH₃ | |
| 2.021 | Me | Cl | CF₃ | —C(O)CH₃ | —C₂H₅ | |
| 2.022 | Me | Cl | —S(O)₂nPr | —CH₃ | —CH₃ | |
| 2.023 | Et | Cl | —S(O)₂Me | —CH₃ | —C₂H₅ | |
| 2.024 | Me | Cl | —S(O)₂Me | —CH₃ | -nPr | 1H NMR (400 MHz, CHLOROFORM-d) δ ppm 11.46 (s, 1H) 8.07 (d, J = 8.19 Hz, 1H) 7.56 (d, J = 8.19 Hz, 1H) 3.76 (t, J = 6.30 Hz, 2 H) 3.41 (s, 3H) 3.26 (s, 3H) 2.52 (s, 3H) 1.61 (dq, J = 14.24, 7.19 Hz, 2 H) 0.91 (m, 3H) |
| 2.025 | Me | Cl | —S(O)₂Me | —CH₃ | -iPr | |
| 2.026 | Me | Cl | —S(O)₂Me | —C₂H₅ | —C₂H₅ | |
| 2.027 | Me | Cl | —S(O)₂Me | —C(O)CH₃ | —C₂H₅ | |
| 2.028 | Me | Cl | —S(O)₂Me | —CH₃ | —C₂H₅ | |
| 2.029 | Me | Cl | —S(O)₂nPr | —CH₃ | —CH₃ | |
| 2.030 | Me | Cl | —S(O)₂Et | —CH₃ | —CH₃ | |
| 2.031 | Me | F | —CF₃ | —C(O)C(CH₃)₃ | —CH₃ | |
| 2.032 | Me | F | —CF₃ | —C(O)CH₃ | —CH₃ | |
| 2.033 | Me | F | —CF₃ | —CH₃ | —CH₃ | |
| 2.034 | Me | Cl | —S(O)₂Me | —CH₃ | -nPr | |
| 2.035 | Et | Cl | —S(O)₂Me | —CH₃ | -iPr | |
| 2.036 | Me | Cl | —S(O)₂Me | —CH₃ | CF₃CH₂— | |
| 2.037 | Me | Cl | —CH₃ | —C(O)nPr | —CH₃ | |
| 2.038 | Me | Cl | —S(O)₂Me | —C(O)iPr | —CH₃ | |
| 2.039 | Me | Cl | —CHF₂ | —C(O)CH₃ | —CH₃ | |
| 2.040 | Me | Cl | —CHF₂ | —CH₃ | —CH₃ | |
| 2.041 | Et | Cl | —S(O)₂Me | —CH₃ | -iPr | |
| 2.042 | Me | Cl | —S(O)₂Me | —CH₃ | CF₃CH₂— | |
| 2.043 | Me | Cl | —CF₃ | —C(O)nPr | —CH₃ | |
| 2.044 | Me | Cl | —S(O)₂Me | —C(O)iPr | —CH₃ | |
| 2.045 | Me | Cl | —CH₃ | —C₂H₅ | —C₂H₅ | |
| 2.046 | Me | C | —CH₃ | —CH₃ | nPr | |
| 2.047 | Me | Cl | —CH₃ | nPr | —CH₃ | |
| 2.048 | Me | Cl | —CF₃CHF₂ | —C(O)CH₃ | —CH₃ | |
| 2.049 | Me | Cl | —CHF₂ | —CH₃ | —CH₃ | |
| 2.050 | Et | Cl | —CHF₂ | —C(O)CH₃ | —CH₃ | |
| 2.051 | n-Pr | Cl | —CHF₂ | —C(O)CH₃ | —CH₃ | |
| 2.052 | Me | —CH₃ | —CHF₂ | —C(O)CH₃ | —CH₃ | |
| 2.053 | Me | Cl | —CHF₂ | —C(O)OC(CH₃)₃ | —CH₃ | |
| 2.054 | Me | Cl | —CHF₂ | —C(O)iPr | —CH₃ | |
| 2.055 | Me | Cl | —CHF₂ | —C(O)C₂H₅ | —CH₃ | |
| 2.056 | Me | Cl | —CHF₂ | —C(O)CH₂CH(CH₃)₂ | —CH₃ | |
| 2.057 | Me | Cl | —CHF₂ | —C(O)CH₃ | —C₂H₅ | |
| 2.058 | Me | Cl | —CHF₂ | —CH₃ | —C₂H₅ | |
| 2.059 | Me | F | —CHF₂ | —C(O)C(CH3)3 | —CH₃ | |
| 2.060 | Me | F | —CHF₂ | —C(O)CH3 | —CH₃ | |
| 2.061 | Me | F | —CHF₂ | —CH₃ | —CH₃ | |
| 2.062 | Me | Cl | —CHF₂ | —C(O)nPr | —CH₃ | |
| 2.063 | Me | Cl | —CHF₂ | —C₂H₅ | —C₂H₅ | |
| 2.064 | Me | Cl | —CHF₂ | —CH₃ | nPr | |
| 2.065 | Me | Cl | —CHF₂ | nPr | —CH₃ | |

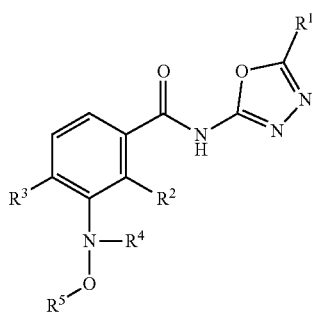

Biological Examples

Seeds of a variety of test species are shown in standard soil in pots (*Lolium perenne* (LOLPE), *Amaranthus retoflexus* (AMARE), *Abutilon theophrasti* (ABUTH), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 500 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

TABLE B2

| Compound | Rate g/ha | POST Application AMARE | POST Application SETFA |
|---|---|---|---|
| 1.001 | 125 | 90 | 90 |

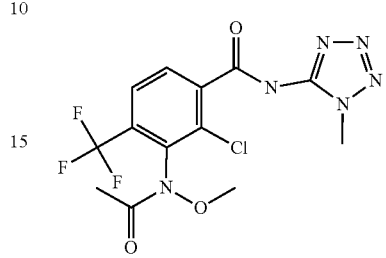

| Compound | Rate g/ha | AMARE | SETFA |
|---|---|---|---|
| 1.043 | 125 | 100 | 90 |

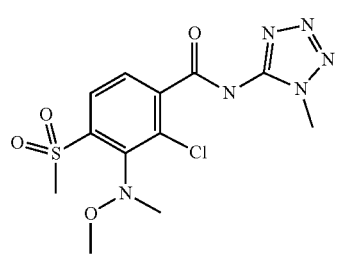

| Compound | Rate g/ha | AMARE | SETFA |
|---|---|---|---|
| 2.002 | 125 | 50 | 90 |

TABLE B1

| Compound | POST AMARE | POST ABUTH | POST SETFA | POST ECHCG | POST IPOHE | PRE AMARE | PRE ABUTH | PRE SETFA | PRE ECHCG | PRE IPOHE |
|---|---|---|---|---|---|---|---|---|---|---|
| 1.001 | 5 | 5 | 5 | 5 | 5 | 5 | 5 | 5 | 5 | 5 |
| 1.007 | 5 | 5 | 5 | 5 | 5 | 5 | 5 | 3 | 5 | 5 |
| 1.008 | 5 | 5 | 5 | 5 | 5 | 5 | 5 | 5 | 5 | 5 |
| 1.009 | 5 | 5 | 5 | 5 | 5 | 5 | 5 | 4 | 5 | 5 |
| 1.025 | 5 | 5 | 5 | 5 | 5 | 5 | 5 | 5 | 5 | 5 |
| 1.031 | 5 | 5 | 5 | 5 | 5 | 5 | 5 | 5 | 5 | 5 |
| 1.037 | 5 | 5 | 5 | 5 | 5 | 5 | 5 | 5 | 5 | 5 |
| 1.043 | 5 | 5 | 5 | 5 | 5 | 5 | 5 | 5 | 5 | 5 |
| 1.044 | 5 | 5 | 5 | 5 | 5 | 5 | 5 | 5 | 5 | 5 |
| 1.045 | 5 | 5 | 5 | 5 | 5 | 5 | 5 | 5 | 5 | 5 |
| 1.049 | 5 | 5 | 5 | 5 | 5 | 5 | 5 | 5 | 5 | 5 |
| 1.050 | 5 | 5 | 5 | 5 | 5 | 5 | 5 | 5 | 5 | 4 |
| 1.054 | 5 | 5 | 5 | 5 | 5 | 5 | 5 | 5 | 5 | 5 |
| 1.055 | 5 | 5 | 5 | 5 | 5 | 5 | 5 | 5 | 5 | 5 |
| 1.056 | 5 | 5 | 5 | 5 | 5 | 5 | 5 | 5 | 5 | 5 |
| 1.057 | 5 | 5 | 5 | 5 | 5 | 5 | 5 | 5 | 5 | 5 |
| 1.061 | 5 | 5 | 5 | 5 | 5 | 5 | 5 | 5 | 5 | 5 |
| 1.062 | 5 | 5 | 5 | 5 | 5 | 5 | 5 | 5 | 5 | 5 |
| 1.063 | 5 | 5 | 5 | 5 | 4 | 5 | 5 | 5 | 5 | 2 |
| 1.065 | 5 | 5 | 5 | 5 | 5 | 5 | 5 | 5 | 5 | 5 |
| 2.001 | 5 | 5 | 5 | 5 | 5 | 5 | 5 | 5 | 5 | 4 |
| 2.002 | 5 | 5 | 5 | 5 | 5 | 5 | 5 | 5 | 5 | 5 |
| 2.009 | 3 | 3 | 5 | 5 | 3 | 5 | 3 | 2 | 5 | 1 |
| 2.018 | 5 | 5 | 5 | 5 | 5 | 5 | 5 | 5 | 5 | 4 |
| 2.024 | 5 | 5 | 5 | 5 | 5 | 5 | 5 | 5 | 5 | 5 |

TABLE B2-continued

| Compound | Rate g/ha | POST Application AMARE | POST Application SETFA |
|---|---|---|---|
| 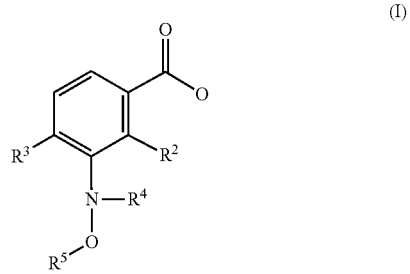 2.024 | 125 | 80 | 80 |
| 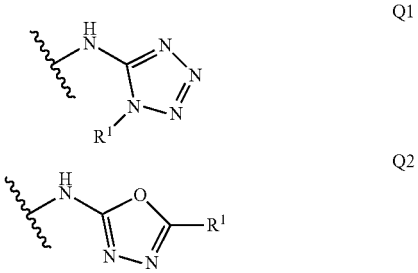 C1 | 125 | 10 | 20 |

A comparative experiment is conducted to show the advantage provided by the compounds of the present invention. Thus the biological performance of representative compounds 1.001, 1.043, 2.002 & 2.024 of the present invention are compared with Compound C1, which is an aniline compound of the type referred to in WO2012/028579. Results are given as (%) phytotoxicity observed. The result demonstrates that compounds of the present invention provide much improved control of problematic weed species, exemplified using *Amaranthus retroflexus* (AMARE) and *Setaria faberi* (SETFA), at similar application rates.

The invention claimed is:

1. A compound of Formula (I):

or an agronomically acceptable salt thereof, wherein:—
Q is selected from the group consisting of Q1 and Q2:

$R^1$ is selected from the group consisting of $C_1$-$C_4$alkyl-, $C_1$-$C_4$haloalkyl- and $C_1$-$C_4$alkoxy-$C_1$-$C_4$alkyl-;
$R^2$ is selected from the group consisting of halogen, $C_1$-$C_6$alkyl-, $C_1$-$C_3$alkoxy-, $C_1$-$C_6$ haloalkyl-, $C_1$-$C_3$haloalkoxy- and —S(O)$_p$$C_1$-$C_6$alkyl;
$R^3$ is selected from the group consisting of halogen, $C_1$-$C_6$alkyl-, $C_1$-$C_3$alkoxy-, $C_1$-$C_6$ haloalkyl-, $C_1$-$C_3$haloalkoxy- and —S(O)$_p$$C_1$-$C_6$alkyl;
$R^4$ is selected from the group consisting of $C_1$-$C_6$alkyl, $C_1$-$C_6$alkyl-C(O)—, $C_1$-$C_6$alkoxy-C(O)—;
$R^5$ is $C_1$-$C_6$alkyl- or $C_1$-$C_6$haloalkyl; and
p=0, 1 or 2.

2. The compound according to claim 1, wherein Q is Q1.
3. The compound according to claim 1, wherein Q is Q2.
4. The compound according to claim 1, wherein $R^1$ is selected from the group consisting of methyl, ethyl and n-propyl.
5. The compound according to claim 1, wherein $R^2$ is halogen.
6. The compound according to claim 5, wherein $R^2$ in chlorine.
7. The compound according to claim 1, wherein $R^3$ is $CF_3$ or —$SO_2CH_3$.
8. The compound according to claim 1, wherein $R^4$ is selected from the group consisting of methyl, $CH_3C(O)$— or $C_1$-$C_4$alkoxyC(O)—.
9. The compound according to claim 1, wherein $R^5$ is methyl.
10. The compound according to claim 1, wherein $R^4$ is $CH_3C(O)$— and $R^5$ is methyl.
11. A herbicidal composition comprising a compound according to claim 1 and an agriculturally acceptable formulation adjuvant.

12. The herbicidal composition according to claim 11, further comprising at least one additional pesticide.

13. The herbicidal composition according to claim 12, wherein the additional pesticide is a herbicide or herbicide safener.

14. A method of controlling weeds at a locus comprising application to the locus of a weed controlling amount of a composition according to claim 11.

* * * * *